United States Patent
Ueno et al.

(10) Patent No.: US 7,351,809 B2
(45) Date of Patent: Apr. 1, 2008

(54) GLYCEROL CARBONATE GLYCOSIDE

(75) Inventors: Katsuya Ueno, Wakayama (JP); Hiromoto Mizushima, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/574,549

(22) PCT Filed: Oct. 1, 2004

(86) PCT No.: PCT/JP2004/014493

§ 371 (c)(1), (2), (4) Date: Jan. 4, 2007

(87) PCT Pub. No.: WO2005/033122

PCT Pub. Date: Apr. 14, 2005

(65) Prior Publication Data

US 2007/0213517 A1    Sep. 13, 2007

(30) Foreign Application Priority Data

Oct. 2, 2003    (JP) ............... 2003-344434

(51) Int. Cl.
C07G 3/00 (2006.01)
C07H 15/00 (2006.01)
C07H 17/00 (2006.01)
A01N 43/04 (2006.01)
A61K 31/70 (2006.01)

(52) U.S. Cl. .................. 536/18.6; 536/18.5

(58) Field of Classification Search ............. None
See application file for complete search history.

(56) References Cited

FOREIGN PATENT DOCUMENTS

| JP | 1-56692 | 3/1989 |
|---|---|---|
| JP | 1-137991 | 5/1989 |
| JP | 6-9674 | 1/1994 |
| JP | 6-80545 | 3/1994 |
| JP | 9-38478 | 2/1997 |
| JP | 9-140393 | 6/1997 |
| JP | 11-222496 | 7/1999 |
| JP | 2001-526106 | 12/2001 |

OTHER PUBLICATIONS

Putman et al. JACS (1954) vol. 76, pp. 2221-2223.*

* cited by examiner

*Primary Examiner*—Patrick Lewis
(74) *Attorney, Agent, or Firm*—Oblon, Spivak, McClelland, Maier & Neustadt, P.C.

(57) ABSTRACT

A process is provided for the selective and convenient production of a glycerol glycoside, which has been glycosidated at the 1-hydroxyl group of glycerol and is useful as a glyceroglycolipid precursor, humectant or the like.

A glycerol carbonate glycoside represented by the following formula (1):

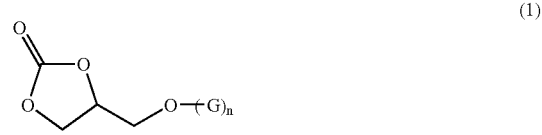

(1)

wherein G represents a monosaccharide residue, and n stands for an integer of from 1 to 3; a process for producing the glycerol carbonate glycoside of formula (1) by reacting a saccharide with glycerol-1,2-carbonate in the presence of an acid; and a process for producing a glycerol glycoside which is represented by the following formula (2):

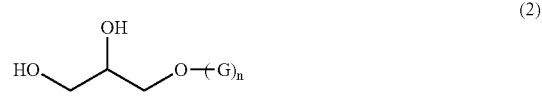

(2)

wherein G and n have the same meanings as defined above, by deprotecting the glycerol carbonate glycoside represented by formula (1).

8 Claims, No Drawings

GLYCEROL CARBONATE GLYCOSIDE

FIELD OF THE INVENTION

This invention relates to a novel glycoside containing a glycerol carbonate as an aglycone, its production process, and a novel process for producing a glycerol glycoside by using the novel glycoside as a precursor.

BACKGROUND OF THE INVENTION

Glycerol glycosides represented by glucosylglycerol, galactosylglycerol and the like are known to exist in plants such as algae (Non-patent Document 1) and fermented foods such as sake, miso (soybean paste) and mirin (sweet cooking sake) (Patent Document 1). These glycerol glycosides are useful as precursors for synthesis of glyceroglycolipids, and their condensation with fatty acids by use of a catalyst such as an acid or an enzyme such as lipase enables synthesis of glyceroglycolipids. Further, these glycerol glycosides have water-retaining property by themselves, and are useful compounds effective for enhancing the stability of emulsions. In Patent Document 2, for example, galactosylglycerol has been substantiated to have water-retaining property and a stability-improving effect on emulsions, and examples of its application to skin cream and face lotion are disclosed.

As a process for obtaining a glycerol glycoside, (1) extraction from a plant or the-like which contains the glycerol glycoside, (2) hydrolysis of a glyceroglycolipid, (3) synthesis from a glycerol donor and a saccharide donor, or the like can be mentioned. When the process (1) is used, the glycerol glycoside exists only in a very little amount in the plant, so that a large amount of plant is required to obtain only a small amount of sample and its purification is complex and requires substantial labor. As the process (2), for example, can be mentioned the process disclosed in Patent Document 3 in which a glycerol glycoside is produced by hydrolyzing naturally-occurring glyceroglycolipids in the presence of an ion-exchange resin. In this process, the glyceroglycolipids used as raw materials are mostly derived from animals or plants, and moreover, the contents of glyceroglycolipids in animals or plants are low. Accordingly, these glyceroglycolipids are very costly, and are not suited for industrial use. The process (3) is widely used to directly glycosidate not only glycerol but also various aglycones. Reactions making use of an acid catalyst, a glycosyltransferase or the like are known. For example, Patent Document 4, Patent Document 5 and Patent Document 6 disclose processes for producing galactosylglycerol by causing various glycosyltransferases to act on a galactose donor such as lactose and a glycerol donor. However, the glycosidation of a polyhydric alcohol such as glycerol is expected to form a mixture of galactosylglycerol glycosidated at the 1-hydroxyl group of glycerol, galactosylglycerol glycosidated at the 2-hydroxyl group of glycerol, and galactosylglycerol glycosidated at plural hydroxyl groups of glycerol, and therefore, selective synthesis is difficult. As many of naturally-existing glyceroglycolipids have a structure in which a saccharide is bonded to the 1-hydroxyl group of glycerol, it is desired to selectively obtain a glycerol glycoside in which the 1-hydroxyl group of glycerol is glycosidated in view of its use as a precursor of a glyceroglycolipid.

As a still further process, a reaction that produces glucosylglycerol from allyl glucoside via its epoxy derivative is disclosed in Non-patent Document 3. However, this process includes many reaction steps and is not considered to be a convenient process. Moreover, Patent Document 7 discloses use of a glyceroglycolipid analogue, which has been substituted at a hydroxyl group in the glycerol moiety and is similar to a glycerol glycoside, as an antiplaque agent. In this prior art document, the glyceroglycolipid is synthesized by a complex, multi-step synthesis process.

Non-patent Document 1: Carbohydr. Res. 73, 193-202, 1979

Non-patent Document 2: J. Am. Chem. Soc., 76, 2221, 1954

Non-patent Document 3: J. Carbohydr. Chem. 17(6), 937-968,

Patent Document 1: JP-A-11-222496

Patent Document 2: JP-A-09-38478

Patent Document 3: JP-B-05-25880

Patent Document 4: JP-B-2527345

Patent Document 5: JP-A-2002-218993

Patent Document 6: JP-A-09-140393

Patent Document 7: JP-A-06-80545

DISCLOSURE OF THE INVENTION

Problem to be Solved by the Invention

This invention relates to a process for selective and convenient production of a glycerol glycoside, particularly a glycerol glycoside in which the 1-hydroxyl group of glycerol is glycosidated, which is useful as a glyceroglycolipid precursor, a humectant or the like.

Means to Solve the Problem

This invention provides a glycerol carbonate glycoside represented by the following formula (1):

[Chemical Formula 1]

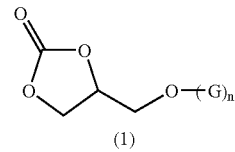

(1)

wherein G represents a monosaccharide residue, and n stands for an integer of from 1 to 3.

This invention also provides a process for production of the glycerol carbonate glycoside of formula (1), which process includes reacting a saccharide with glycerol-1,2-carbonate in the presence of an acid.

This invention further provides a process for production of a glycerol glycoside represented by the following formula (2):

[Formula 2]

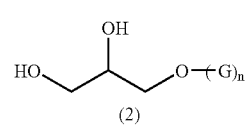

(2)

wherein G represents a monosaccharide residue, and n stands for an integer of from 1 to 3, which process includes deprotecting the glycerol carbonate glycoside represented by formula (1).

EFFECTS OF THE INVENTION

By the present invention, a novel glycerol carbonate glycoside can be produced. In addition, a glycerol glycoside in which the 1-hydroxyl group of glycerol is glycosidated can be produced selectively in a good yield from the glycerol carbonate glycoside.

MODES FOR CARRYING OUT THE INVENTION

The present inventors have conducted an extensive investigation to provide a process for selective and convenient production of a glycerol glycoside. As a result, it has been found that only the 1-hydroxyl group of the glycerol skeleton can be selectively glycosidated by glycosidating glycerol-1,2-carbonate, which is a 1,2-protected cyclic carbonate, as an aglycone in the presence of an acid, and also that use of the thus-obtained glycoside as a raw material can give a glycerol glycoside in which the 1-hydroxyl group of glycerol is selectively glycosidated. When a raw material having an ester group is reacted in the presence of an acid, there is a potential problem of cleavage of the ester group as a side reaction since an ester bond is generally weak to an acid. It has, however, been surprisingly found that under the reaction conditions according to the present invention, the cleavage of a carbonate ester is minimized even in the presence of an acid. As a result of a search, it has been ascertained that each glycerol carbonate glycoside obtained according to the present invention has not been reported to date and, therefore, is a novel compound. Further, each glycerol carbonate glycoside obtained according to the present invention can be readily deprotected by making a base or the like act thereon and can be converted in a high yield into a target glycerol glycoside.

The glycerol carbonate glycoside obtained according to the present invention and represented by the formula (1) is a novel glycoside.

The monosaccharide corresponding to the monosaccharide residue represented by G in formulas (1) and (2) may have any structure insofar as it is a monosaccharide capable of forming a glycoside bond. Examples thereof include hexoses such as glucose, galactose, mannose, talose, fructose, sorbose, tagatose and psicose; pentoses such as arabinose, xylose, ribose and lyxose; deoxysugars such as deoxyribose, rhamnose, fucose (rhodeose) and isorhodeose; aminosugars such as glucosamine, galactosamine, glosamine, sialic acid (neuramic acid) and muramic acid, and N-acetylated derivatives thereof;—and uronic acids such as glucuronic acid, galacturonic acid, mannuronic acid, iduronic acid and gluronic acid. In these monosaccharide residues, their hydroxyl groups may be converted into sulfate esters, phosphate esters, acetate esters, benzyl ethers, silyl ethers, and the like. When two or more monosaccharide residues are contained in a molecule ($n \geq 2$ in formula (1)), such monosaccharide residues may all be residues of the same kind of saccharides, or different saccharides maybe bonded. On the other hand, n in formulas (1) and (2) stands for an integer of from 1 to 3, with 1 being preferred. The compounds of formulas (1) and (2) are each glycosidated via a glycoside bond with the monosaccharide residue represented by G.

Glycerol-1,2-carbonate employed as one of the raw materials for the synthesis of glycerol carbonate glycoside in the present invention is sold on the market, and is readily available. Alternatively, it can be synthesized by reacting a carbonyl compound such as dimethyl carbonate, phosgene or urea with glycerol.

The saccharide used as the other raw material for the synthesis of glycerol carbonate glycoside in the present invention may have any structure insofar as it is a saccharide capable of forming a glycoside bond. It is possible to use not only a monosaccharide but also an oligosaccharide such as a disaccharide or trisaccharide.

As the acid employed in the production of the glycerol carbonate glycoside, Lewis acids such as boron trifluoride, Brønsted acids such as paratoluenesulfonic acid, sulfuric acid, hydrochloric acid and phosphomolybdic acid, solid acids such as alumina, montmorillonite and zeolite, and hydrates and solvates and the like of these acids can be mentioned. Preferred are boron trifluoride, paratoluenesulfonic acid, and the hydrates or solvates of these acids, with solvates of boron trifluoride, for example, $BF_3 \cdot OEt_2$ being more preferred. No particular limitation is imposed on the amount of the acid to be used insofar as the acid is added in an amount sufficient to produce the glycerol carbonate glycoside. In general, however, the acid can be used in an amount of from 0.1 to 10 molar times that of glycerol-1,2-carbonate. An organic solvent such as dichloromethane may be used as a solvent, although no solvent may be used.

In the production of the glycerol carbonate glycoside, the reaction temperature can be set depending on the reactivity of the saccharide as a raw material and the catalyst, within a range not causing the decomposition of the carbonate. In general, however, the reaction temperature is in a range of from 0° C. to 150° C., with a range of from 0 to 100° C. being preferred. A reaction temperature not higher than 100° C. can inhibit any pronounced decomposition of the carbonate, while a reaction temperature not lower than 0° C. is preferred from the standpoint of reaction velocity.

In the production of the glycerol carbonate glycoside, the charge ratio (molar ratio) of the saccharide to glycerol-1,2-carbonate can be optionally set. It is, however, a common practice to charge glycerol-1,2-carbonate as an aglycone in a small excess. The charge ratio of glycerol-1,2-carbonate to the saccharide (the molar ratio of glycerol-1,2-carbonate to the saccharide) is preferably from 1.0 to 10.0, more preferably from 1.0 to 5.0. When the saccharide to be used is an unprotected saccharide, the saccharide hardly undergoes mutual condensation if the charge ratio is not less than 1.0. A ratio of not more than 10.0, on the other hand, is economical because unreacted glycerol-1,2-carbonate does not remain in a large amount.

When deprotected, the glycerol carbonate glycoside can be converted into the target glycerol glycoside in a high yield. As a deprotecting agent, a base or a reducing agent is usually employed. Any base or reducing agent can be used insofar as it can cleave the cyclic carbonate without affecting the glycoside bond. Examples include, but are not limited to, bases such as alkali metal alkoxides such as sodium methoxide and sodium ethoxide, and alkali metal hydroxides such as sodium hydroxide and potassium hydroxide; and reducing agents such as lithium aluminum hydride and sodium bis(2-methoxyethoxy) aluminum hydride. A preferred deprotecting agent is sodium methoxide.

The amount of the base or reducing agent to be used can be optionally set. A preferred amount of the base or reducing agent can be from 1.00 to 5.0 equivalents, particularly from 1.0 to 2.0 equivalents per the ester bond of the glycerol carbonate glycoside. An amount of not less than 1.0 equivalent results in no remaining unreacted ester bond, and an amount of not more than 5.0 equivalents is preferred from an economical viewpoint.

As the solvent for the above-described deprotection, methanol, ethanol, isopropanol, tetrahydrofuran, 1,3-dioxane or the like can be used.

In the production of the glycerol glycoside by deprotecting the glycerol carbonate glycoside, the reaction temperature can be optionally set, depending on the kind of the base or the like to be used, within a range not causing the cleavage of the glycoside bond. From the viewpoints of inhibition of the cleavage of the glycoside bond and an adequate reaction velocity, however, a range of from 0 to 100° C. is preferred in general.

EXAMPLES

The present invention will hereinafter be specifically described in detail by way of the following examples. The reaction rate (percentage of reaction) in each example was calculated from the remaining amount (area %) of the raw material saccharide as determined by gas chromatography (GC). Yields are all by molar %.

Example 1

[Chemical Formula 3]

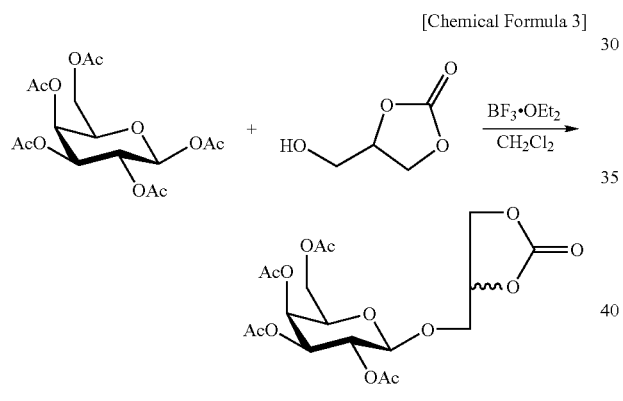

In a 300-mL eggplant type flask, β-D-pentaacetylgalactose (9.77 g) and glycerol-1,2-carbonate (4.43 g) were charged, followed by dissolution in dichloromethane (100 mL). Into the solution, $BF_3 \cdot OEt_2$ (14.20 g) was added dropwise with stirring at room temperature under a nitrogen atmosphere. Subsequent to stirring at room temperature for 2 hours, a saturated aqueous solution (200 mL) of $NaHCO_3$ was added to terminate the reaction. The reaction mixture was transferred into a separatory funnel, a dichloromethane layer was separated, and an aqueous layer was extracted with dichloromethane (100 mL×2). The dichloromethane solutions were combined together and were dried over anhydrous sodium sulfate. After sodium sulfate was removed by filtration, dichloromethane was eliminated under reduced pressure. As a result of the GC analysis of the resultant viscous oil, the reaction rate of the saccharide was 94%. By purifying the viscous oil through a silica gel column (developer: hexane/ethyl acetate), a white solid was obtained (8.59 g) As a result of the analysis by $^1$HNMR, the solid was found to be a 1:1 mixture of diastereomers different in the configuration at the 2-position in the glycerol skeleton of the target β-D-tetraacetylgalactosyl-1,2-glycerol carbonate (one of the diastereomers will hereinafter be referred to as "diastereomer A", and the other as "diastereomer B"). Its yield was 77%. A portion of the solid was fractionated further through a silica gel column to isolate the respective diastereomers from each other, and their detailed structures were determined by $^1$HNMR, $^1$H—$^1$H COSY and MS analysis.

Diastereomer A $^1$HNMR (400 MHz, $CDCl_3$) δ5.41(dd, J=3.4 Hz, 1.0 Hz, 1H), 5.23(dd, J=10.4 Hz, 8.0 Hz, 1H), 5.02(dd, J=10.6 Hz, 3.4 Hz, 1H), 4.84(m, 1H), 4.58(d, J=8.0 Hz, 1H), 4.48(d, J=7.6 Hz, 2H), 4.19(dd, J=11.2 Hz, 6.4 Hz, 1H), 4.12(dd, J=11.0 Hz, 6.6 Hz, 1H), 3.99(dd, J=12.0 Hz, 2.4 Hz, 1H), 3.94(td, J=6.8 Hz, 1.2 Hz, 1H), 3.90(dd, J=12.2 Hz, 3.0 Hz, 1H), 2.16(s, 3H), 2.10(s, 3H), 2.06(s, 3H), 1.99(s, 3H).

$^{13}$CNMR (400 MHz, $CDCl_3$) δ170.4, 170.1, 170.0, 169.8, 154.6, 101.5, 74.4, 70.9, 70.5, 68.2, 67.6, 66.9, 65.5, 61.1, 20.6, 20.6, 20.5, 20.5.

MS m/z=449.0 (M+H$^+$).

Diastereomer B $^1$HNMR (400 MHz, $CDCl_3$) δ5.40(dd, J=3.2 Hz, 1.2 Hz, 1H), 5.22(dd, J=10.8 Hz, 8.0 Hz, 1H), 5.02(dd, J=10.6 Hz, 3.4 Hz, 1H), 4.83(m, 1H), 4.57(d, J=8.0 Hz, 1H), 4.52(t, J=8.6 Hz, 1H), 4.34(dd, J=8.4 Hz, 6.4 Hz, 1H), 4.18(dd, J=11.7 Hz, 6.8 Hz, 1H), 4.13(dd, J=11.4 Hz, 6.8 Hz, 1H), 4.05(dd, J=11.4 Hz, 4.2 Hz, 1H), 3.95(td, J=6.8 Hz, 1.2 Hz, 1H), 3.81(dd, J=11.2 Hz, 4.8 Hz, 1H), 2.17(s, 3H), 2.09(s, 3H), 2.06(s, 3H), 1.99(s, 3H).

$^{13}$CNMR (400 MHz, $CDCl_3$) δ170.4, 170.1, 170.0, 169.5, 154.5, 101.1, 74.5, 71.0, 70.6, 68.2, 68.1, 66.8, 66.0, 61.1, 20.7, 20.6, 20.6, 20.5.

MS m/z=449.0 (M+H$^+$).

Example 2

[Chemical Formula 4]

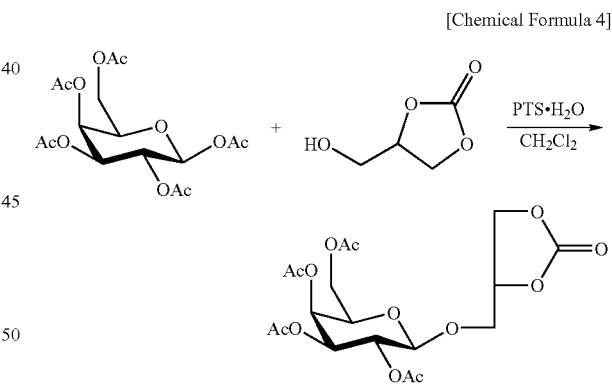

In a 100-mL eggplant type flask, β-D-pentaacetylgalactose (3.90 g), glycerol-1,2-carbonate (1.77 g) and paratoluenesulfonic acid monohydrate ($PTS \cdot H_2O$, 0.19 g) were charged, followed by dissolution in dichloromethane (40 mL). The solution was heated and refluxed with stirring. After 15 hours, the solution was allowed to cool down to room temperature, and a saturated aqueous solution (100 mL) of $NaHCO_3$ was added. The reaction mixture was transferred into a separatory funnel, a dichloromethane layer was separated, and an aqueous layer was extracted with dichloromethane (50 mL×2). The dichloromethane solutions were combined together and were dried over anhydrous sodium sulfate. After sodium sulfate was removed by filtration, the dichloromethane was eliminated under reduced pressure. As a result of the GC analysis of the resultant viscous oil, the reaction rate of the saccharide was 70%. By purifying the viscous oil through a silica gel column (developer: hexane/ethyl acetate), β-D-tetraacetylgalactosyl-1,2-glycerol carbonate (a 1:1 mixture of diastereomer A and diastereomer B; 0.80 g) was afforded (yield: 18%).

Example 3

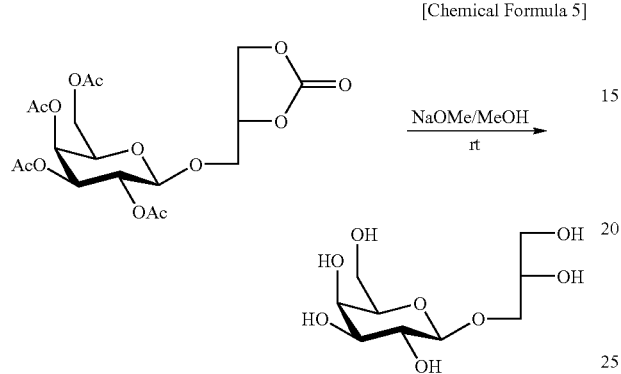

In a 100-mL eggplant type flask, β-D-tetraacetylgalactosyl-1,2-glycerol carbonate (diastereomer A; 0.5 g) obtained in Example 1 was dissolved in absolute methanol (10 mL). Under a nitrogen atmosphere, a solution (1.67 g) of sodium methoxide (NaOMe) in 28% methanol (MeOH) was added to the solution, followed by stirring for 30 minutes at room temperature (rt). The reaction mixture was transferred into a column packed with "AMBERLITE IR-118(H)" (product of Rhom and Haas Company; 19.4 mL; the resin had been thoroughly washed beforehand with distilled water and methanol), and was allowed to pass through the column at a flow rate of about 1 mL/min. Subsequently, the resin was washed with methanol (150 mL). The eluate and the washing were combined. Subsequent to elimination of methanol under reduced pressure, distilled water (5 mL) was added thereto and the insoluble matter was collected by filtration through a membrane filter. The filtrate was lyophilized to afford a single diastereomer of β-D-galactosylglycerol (hereinafter referred to as "diastereomer a"; 0.18 g; yield: 64%).

Diastereomer a:
$^{13}$CNMR (400 MHz, D$_2$O) δ105.9, 78.0, 75.5, 73.7, 73.6, 73.3, 71.5, 65.2, 63.9.
MS m/z=255.0 (M+H$^+$).

Example 4

A reaction was conducted in a similar manner as in Example 4 except that in Example 3, the raw material was changed to β-D-tetraacetylgalactosyl-1,2-glycerol carbonate (diastereomer B) obtained in Example 1. As a result, a single diastereomer of β-D-galactosylglycerol (hereinafter referred to as "diastereomer b"; 0.18 g; yield: 64%) was afforded.

Diastereomer b:
$^{13}$CNMR (400 MHz, D$_2$O) δ106.2, 78.0, 75.5, 73.8, 73.7, 73.5, 71.5, 65.2, 63.9.
MS m/z=255.0 (M+H$^+$).

The invention clamed is:
1. A glycerol carbonate glycoside represented by the following formula (1):

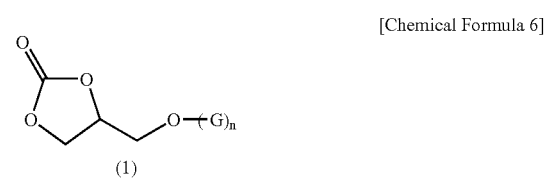

wherein G represents a monosaccharide residue, and n stands for an integer of from 1 to 3.

2. A glycerol carbonate glycoside according to claim 1, wherein in the formula (1), n is 1.

3. A process for production of a glycerol carbonate glycoside according to claim 1 or 2, which comprises reacting a saccharide with glycerol-1,2-carbonate in the presence of an acid.

4. The process according to claim 3, wherein said acid is boron trifluoride.

5. A process for production of a glycerol glycoside represented by the following formula (2):

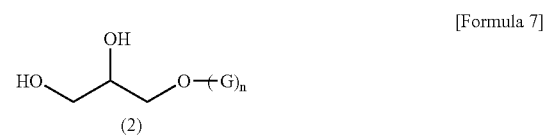

wherein G represents a monosaccharide residue, and n stands for an integer of from 1 to 3, which comprises deprotecting the glycerol carbonate glycoside according to claim 1 or 2.

6. The process according to claim 5, wherein in the formula (2), n is 1.

7. The process according to claim 5 or 6, wherein said deprotection is conducted using a base or reducing agent.

8. The process according to claim 5 or 6, wherein said deprotection is conducted using sodium methoxide.

* * * * *